United States Patent [19]

Weber

[11] Patent Number: 4,482,496
[45] Date of Patent: Nov. 13, 1984

[54] STILBENE COMPOUNDS

[75] Inventor: Kurt Weber, Basle, Switzerland

[73] Assignee: Ciba-Geigy Corporation, Ardsley, N.Y.

[21] Appl. No.: 383,853

[22] Filed: Jun. 1, 1982

[30] Foreign Application Priority Data

Jun. 12, 1981 [CH] Switzerland .................. 3880/81

[51] Int. Cl.³ ........................................ C07C 121/78
[52] U.S. Cl. ........................ 260/465 E; 260/944; 560/27; 560/35; 562/440; 564/256; 544/239; 546/115; 546/119; 548/144; 548/179; 548/224; 548/259; 548/260; 548/241; 548/334
[58] Field of Search .................. 260/465 E, 944; 542/459, 460, 462, 463, 464; 560/35, 27; 564/256; 562/440

[56] References Cited

U.S. PATENT DOCUMENTS 4,108,887 8/1978 Fleck et al. .................. 260/465 H Primary Examiner—Dolph H. Torrence
Attorney, Agent, or Firm—Edward McC. Roberts

[57] ABSTRACT

The invention relates to stilbene compounds of the formula

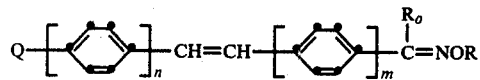

wherein Q is hydrogen; a monocyclic 5- or 6-membered aromatic heterocyclic ring which is unsubstituted or substituted by non-chromophoric groups and which contains no fused benzene rings or one or two fused benzene rings; a bicyclic 9-membered aromatic heterocyclic ring or the radical —CH=C($R_1$)($R_2$), in which $R_1$ is hydrogen, $C_1$-$C_6$alkyl which is unsubstituted or substituted by non-chromophoric groups, and $R_2$ is alkoxycarbonyl containing altogether 2 to 7 carbons atoms, cyano, carboxyl, carbamoyl, phosphonic acid dialkyl ester, $C_1$-$C_6$alkyl or arylsulfonyl; or Q may also be

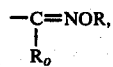

$R_o$ is hydrogen or $C_1$-$C_6$alkyl, R is $C_1$-$C_6$alkyl which is unsubstituted or substituted by non-chromophoric groups, $C_2$-$C_5$alkenyl, $C_2$-$C_5$alkynyl, di($C_1$-$C_4$)alkylamino($C_1$-$C_4$)alkyl, $C_1$-$C_4$hydroxyalkyl, $C_1$-$C_4$phenylalkyl or cycloalkyl containing 5 to 12 ring members, and each of m and n independently of the other is 1 or 2. These compounds may be used for whitening manmade, regenerated manmade and natural organic material of high molecular weight.

7 Claims, No Drawings

STILBENE COMPOUNDS

The present invention relates to novel stilbene compounds, to the production thereof, and to the use thereof for whitening natural and synthetic organic material.

Stilbene compounds are known e.g. from U.S. Pat. No. 3,984,399. It is the object of the present invention to provide novel fluorescent whitening agents having improved exhaustion properties. It has now been found that specific stilbene compounds containing a p-(oxime ether) radical are more productive than stilbene compounds of the prior art.

The novel stilbene compounds have the formula

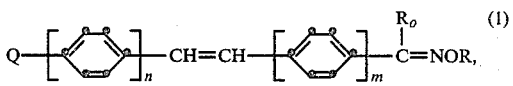

wherein Q is hydrogen; a monocyclic 5- or 6-membered aromatic heterocyclic ring which is unsubstituted or substituted by non-chromophoric groups and which contains no fused benzene rings or one or two fused benzene rings; a bicyclic 9-membered aromatic heterocyclic ring or the radical —CH=C($R_1$)($R_2$), in which $R_1$ is hydrogen, $C_1$–$C_6$alkyl which is unsubstituted or substituted by non-chromophoric groups, and $R_2$ is alkoxycarbonyl containing altogether 2 to 7 carbon atoms, cyano, carboxyl, carbamoyl, phosphonic acid dialkyl ester, $C_1$–$C_6$alkyl or arylsulfonyl; or Q may also be

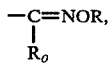

$R_o$ is hydrogen or $C_1$–$C_6$alkyl, R is $C_1$–$C_6$alkyl which is unsubstituted or substituted by non-chromophoric groups, $C_2$–$C_5$alkenyl, $C_2$–$C_5$alkynyl, di($C_1$–$C_4$)alkylamino($C_1$–$C_4$)alkyl, $C_1$–$C_4$hydroxyalkyl, $C_1$–$C_4$phenylalkyl or cycloalkyl containing 5 to 12 ring members, and each of m and n independently of the other is 1 or 2.

Examples of non-chromophoric substituents are: halogen, unsubstituted or substituted alkyl, unsubstituted or substituted alkenyl, aryl or aralkyl, unsubstituted or substituted alkoxy, alkoxycarbonyl, unsubstituted or substituted aminocarbonyl, cyano, alkylsulfonyl, alkoxysulfonyl, unsubstituted or substituted aminosulfonyl, acyl, acylamino, aryloxy, aralkyloxy, alkenyloxy, aryloxycarbonyl, aralkyloxycarbonyl, carboxyl, acyloxy or trifluoromethyl.

Alkyl is preferably $C_1$–$C_4$alkyl which may be monosubstituted by hydroxyl, $C_1$–$C_4$alkoxy, cyano, carboxyl, $C_2$–$C_5$-alkoxycarbonyl, aminocarbonyl, or chlorine.

Alkenyl is preferably $C_2$–$C_5$alkenyl which may be monosubstituted by hydroxyl, $C_1$–$C_4$alkoxy, cyano, carboxyl, $C_1$–$C_4$alkoxycarbonyl or chlorine.

Halogen is preferably fluorine, chlorine or bromine, with chlorine being most preferred.

Aryl is preferably phenyl or phenyl which is substituted by $C_1$–$C_4$alkyl, chlorine, bromine or $C_1$–$C_4$alkoxy.

Aralkyl is preferably $C_1$–$C_4$phenylalkyl which may be additionally substituted in the phenyl nucleus by chlorine, methyl or methoxy.

Alkoxy is preferably $C_1$–$C_4$alkoxy or a radical of the formula —(OCH$_2$—CH$_2$)$_p$—OY, wherein Y is hydrogen or $C_1$–$C_4$alkyl and p is an integer from 1 to 20.

Acyl is preferably $C_2$–$C_5$alkanoyl, $C_1$–$C_4$alkylsulfonyl, benzoyl which is unsubstituted or substituted by chlorine, methyl or methoxy, or phenylsulfonyl which is unsubstituted or substituted by chlorine, methyl or methoxy.

Preferred substitutents of the aminocarbonyl and aminosulfonyl radicals are $C_1$–$C_4$alkyl, phenyl, $C_1$–$C_4$phenylalkyl or phenyl which is substituted by chlorine, methyl or methoxy.

Possible aromatic heterocyclic rings are: benzoxazole, benzimidazole, v-triazole, 1,3,4-oxdiazole, pyrimidine, pyridazinone, pyrazine, s-triazine, 1,3,4-oxdiazolone, 1,2,4-oxdiazole, pyrazole, isoxazole, benzisoxazole, oxazolo[5,4-b]pyridine, oxazolo[5,4-e]pyridine, and 1,2,4-triazolo[1,5-a]pyridine.

Possible substituents of benzoxazole and benzimidazole rings are chlorine, $C_1$–$C_4$alkyl, $C_1$–$C_3$phenylalkyl, cyclohexyl, phenyl, $C_1$–$C_4$alkoxy, $C_1$–$C_4$alkylsulfonyl, $C_1$–$C_4$alkoxycarbonyl, cyano or carboxyl, or, together with a second substituent, a fused cyclopentane, cyclohexane or benzene ring which is unsubstituted or substituted by 1 to 4 methyl groups. Benzimidazole radicals may be additionally substituted in the 1-position by $C_1$–$C_4$alkyl or phenyl.

v-Triazolyl radicals may be substituted by one or two $C_1$–$C_4$alkyl radicals, a $C_1$–$C_4$chloroalkyl radical, a $C_1$–$C_4$alkoxy radical, a cyano group, a COO—$C_1$–$C_4$alkyl radical, one or two phenyl radicals or one styryl radical. The v-triazolyl radical may also contain a fused benzene ring which is unsubstituted or substituted by $C_1$–$C_4$alkoxy, or a fused naphthalene ring.

1,2,4- and 1,3,4-Oxidazole radicals may be substituted by unsubstituted $C_1$–$C_4$alkyl, $C_1$–$C_4$alkyl which is substituted by non-chromophoric groups or phenyl, styryl, biphenylyl or naphthyl, each unsubstituted or substituted by $C_1$–$C_4$alkyl, $C_1$–$C_4$alkoxy, $C_1$–$C_4$alkoxycarbonyl, cyano or chlorine.

Pyrimidine radicals may be unsubstituted or substituted. Examples of possible substituents are: $C_1$–$C_4$alkyl, phenyl or phenyl which is substituted by chlorine or methyl; $C_1$–$C_4$alkoxy, $C_3$–$C_8$alkoxyalkoxy, phenoxy or phenoxy which is substituted by chlorine or methyl; chlorine, $C_1$–$C_4$alkylthio, phenylthio, $C_1$–$C_4$alkylamino, $C_1$–$C_4$dialkylamino, morpholino, piperidino, piperazino, pyrrolidino or anilino.

A pyridazinone radical may be substituted in the 3-position by $C_1$–$C_4$alkyl or by phenyl or phenyl which is substituted by chlorine or methyl.

Pyrazine radicals may be unsubstituted or substituted in the 5-position by e.g. $C_1$–$C_4$alkoxy, $C_3$–$C_8$alkoxyalkoxy, $C_1$–$C_4$alkylthio, phenoxy or phenylthio, which is unsubstituted or substituted by chlorine or methyl; $C_1$–$C_4$alkylamino, $C_1$–$C_4$dialkylamino, morpholino, piperidino, piperazino, pyrrolidino or anilino.

Examples of possible substituents of s-triazine radicals are: halogen, $C_1$–$C_4$alkyl, $C_1$–$C_4$alkoxy, phenyl, aralkoxy, cycloalkoxy, aryloxy, especially phenoxy, $C_1$–$C_4$alkylmercapto, $C_1$–$C_4$alkylamino, $C_1$–$C_4$dialkylamino, morpholino, piperidino, piperazino, pyrrolidino or arylamino, especially phenylamino.

A 1,2,4-oxdiazolone radical may be substituted by $C_1$–$C_4$alkyl or phenyl or phenyl which is substituted by $C_1$–$C_4$alkyl, halogen or cyano.

Pyrazole radicals contain an unsubstituted phenyl radical or a phenyl radical which is substituted by chlorine or $C_1$–$C_4$alkyl, and may be additionally substituted by a $C_1$–$C_4$alkyl radical.

Isoxazole radicals are substituted by an unsubstituted or a $C_1$–$C_4$alkoxy-substituted phenyl radical.

Possible cycloalkyl radicals R are in particular cyclopentyl, cyclohexyl and cycloheptyl.

Interesting compounds within the scope of the formula I are those of the formula

(2)

wherein R' is $C_1$–$C_4$alkyl, $C_1$–$C_4$cyanoalkyl, $C_1$–$C_4$alkoxy-$C_2$–$C_4$alkyl, $C_3$–$C_4$alkenyl, $C_3$–$C_4$alkynyl or $R_x$OOC—$C_1$–$C_4$alkyl, in which $R_x$ is hydrogen or $C_1$–$C_4$alkyl, and $Q_1$ is phenyl or the radical —CH=C($R_1'$)($R_2'$),

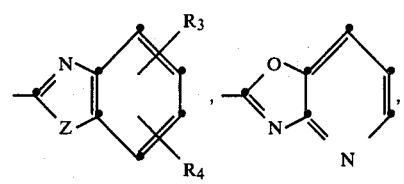

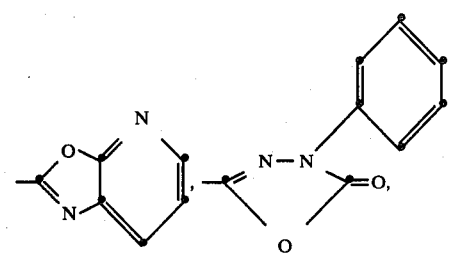

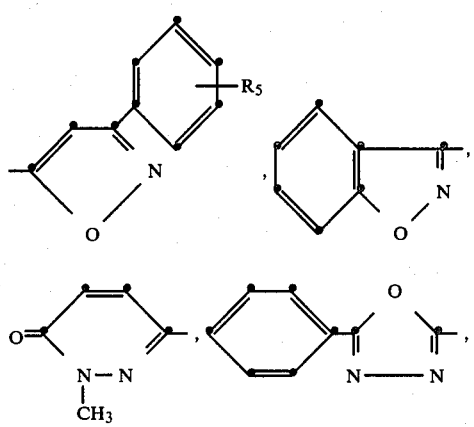

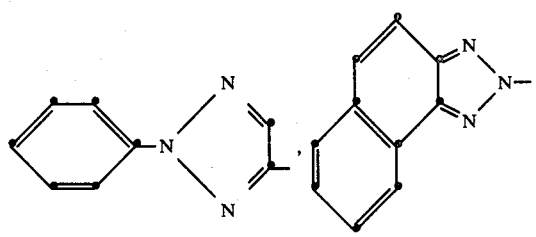

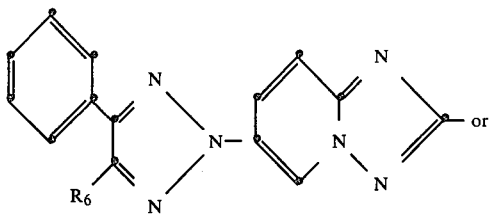

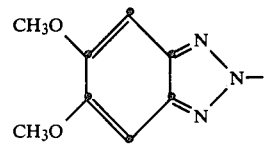

wherein $R_1'$ is hydrogen or $C_1$–$C_4$alkyl, $R_2'$ is alkoxycarbonyl containing altogether 2 to 5 carbon atoms, cyano, carboxyl, carbamoyl, $C_1$–$C_4$alkylsulfonyl or phenylsulfonyl, $R_3$ is hydrogen, chlorine, $C_1$–$C_4$alkyl, $C_1$–$C_3$phenylalkyl, cyclohexyl, phenyl, $C_1$–$C_4$alkoxy, $C_1$–$C_4$alkylsulfonyl, $C_2$–$C_5$alkoxycarbonyl, cyano or carboxyl or, together with $R_4$, is a fused cyclopentane, cyclohexane or benzene ring, each of which is unsubstituted or substituted by 1 to 4 methyl groups; $R_4$ is hydrogen, chlorine, $C_1$–$C_4$alkyl or $C_1$–$C_4$alkoxy or, together with $R_3$, is a fused cyclopentane, cyclohexane or benzene ring, each of which is unsubstituted or substituted by 1 to 4 methyl groups; $R_5$ is hydrogen or methoxy; $R_6$ is hydrogen, $C_1$–$C_4$alkyl or alkoxycarbonyl containing altogether 2 to 5 carbon atoms; and Z is O, S or NX, wherein X is hydrogen, $C_1$–$C_4$alkyl or phenyl.

Preferred stilbene compounds are those of the formula

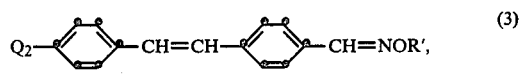
(3)

wherein R' is as defined above and $Q_2$ is the radical —CH=C($R_1'$)($R_2''$),

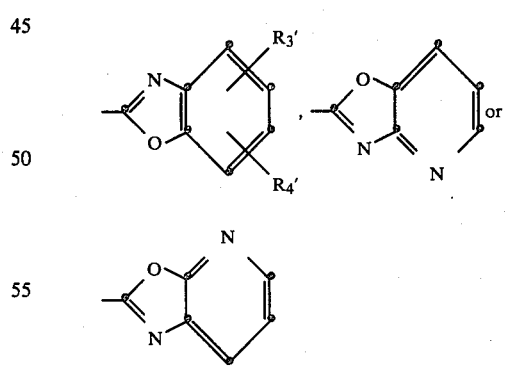

wherein $R_1'$ is hydrogen or $C_1$–$C_4$alkyl, $R_2''$ is alkoxycarbonyl containing altogether 2 to 5 carbon atoms or is cyano, $R_3'$ is hydrogen, $C_1$–$C_4$alkyl, $C_1$–$C_4$alkoxy or alkoxycarbonyl containing altogether 2 to 5 carbon atoms or, together with $R_4'$, is a fused benzene ring, and $R_4'$ is hydrogen or $C_1$–$C_4$alkyl or together with $R_3'$ is a fused benzene ring.

Further preferred compounds of the formula (1) are those of the formula

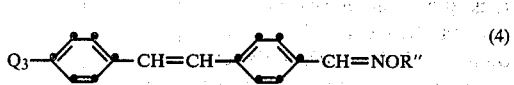

wherein R" is $C_1$-$C_4$alkyl, $C_1$-$C_4$alkoxy-$C_2$-$C_4$alkyl or $C_3$-$C_4$alkenyl, and $Q_3$ is the radical —CH=CH—CN, —CH=CH—COO—$C_1$-$C_4$alkyl or the radical

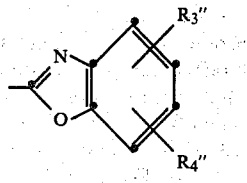

wherein $R_3''$ is hydrogen, $C_1$-$C_4$alkyl, $C_1$-$C_4$alkoxy or $C_2$-$C_5$alkoxycarbonyl, and $R_4''$ is hydrogen or $C_1$-$C_4$alkyl.

Particularly preferred compounds are those of the formula

wherein R''' is —$CH_3$, —$C_2H_5$, —$CH_2CH_2OCH_3$ or —$CH_2$—CH=$CH_2$ and $Q_4$ is the radical —CH=CH—CN, —CH=CH—COO—$C_1$-$C_2$alkyl or

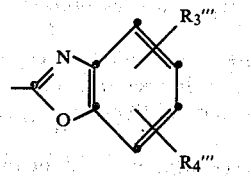

wherein $R_3'''$ is hydrogen or $C_1$-$C_4$alkyl and $R_4'''$ is hydrogen or $C_1$-$C_4$alkyl; and, especially, those of the formulae

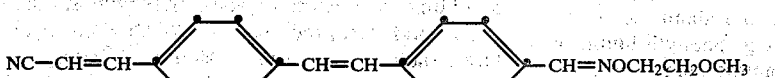

and

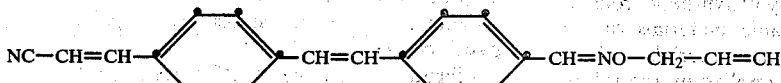

The stilbene compounds of the formula (1) may be obtained by reacting a carbonyl compound of the formula

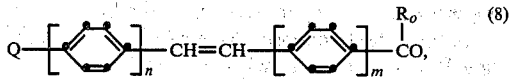

wherein Q, m and n are as defined above, with an O-substituted hydroxylamine of the formula $H_2NOR$      (9)

wherein R has the meaning assigned to it above, said reaction being conducted in an organic solvent which is inert to the reactants.

Instead of using the free bases of the formula (9), their salts may also be used, preferably those with a hydrohalic acid, especially HCl, in the presence of a compound which liberates the free base, e.g. sodium acetate.

Examples of suitable organic solvents are alcohols such as methanol, ethanol, isopropanol, butanol, glycol, glycol ethers such as 2-methoxyethanol, ethylene glycol monomethyl ether, ethylene glycol monoethyl ether, diethylene glycol monomethyl, dimethyl, monoethyl and diethyl ether, cyclohexanol, cyclooctanol, and also ethers such as diisopropyl ether, dioxan, tetrahydrofuran, as well as formamides or N-methylpyrrolidone.

The O-substituted hydroxylamines of the formula (9) are known compounds or they can be prepared by methods which are known per se, e.g. as described in Houben-Weyl, Vol. X/1, pp. 1181 ff. (1971).

The reaction is preferably carried out in the temperature range from 0° C. to the boiling point of the solvent employed.

It will readily understood that further per se known conversions of the reaction products of the above process may be performed, e.g. halogenations, functional modifications of carboxyl groups, introduction of chloromethyl groups or replacement of halogen atoms by cyano groups.

The stilbene compounds of the formula (1) may also be obtained by reacting one mole of a compound of the formula

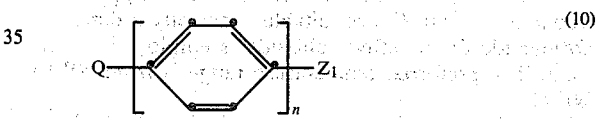

with one mole of a compound of the formula

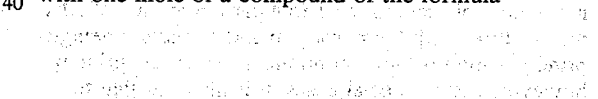

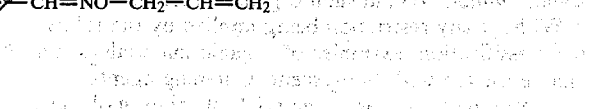

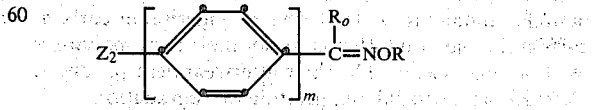

in the presence of a strong base and of a polar solvent, in which formulae Q, n, $R_o$, R and m are as defined above and one of the symbols $Z_1$ and $Z_2$ is a HOC group and the other is a group of the formula

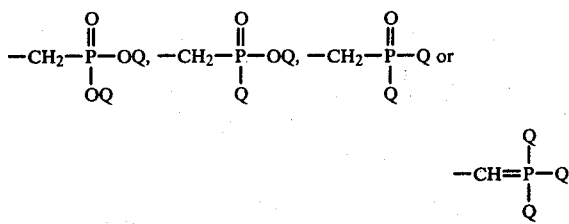

wherein Q is an unsubstituted or substituted alkyl radical of 1 to 6 carbon atoms, an aryl radical, preferably a phenyl radical, a cycloalkyl radical, preferably a cyclohexyl radical, or an aralkyl radical, preferably a benzyl radical.

Suitable solvents are e.g. alcohols such as methanol, ethanol, isopropanol, butanol, glycols, glycol ethers such as 2-methoxyethanol, hexanols, cyclohexanol and cyclooctanol, and also ethers such as diisopropyl ether, tetrahydrofuran and dioxan, as well as dimethyl sulfoxide, formamide and N-methylpyrrolidone. Particularly suitable solvents are polar organic solvents such as dimethyl formamide and dimethyl sulfoxide. Some of the reactions may also be carried out in aqueous solution.

The temperature at which the reaction is conducted may vary within wide limits and depends on:

(α) the stability of the solvent employed to the reactants, especially to the strongly basic alkali metal compounds, (β) the reactivity of the condensation partners, and (γ) the effectiveness of the combination of solvent and base as condensing agent.

In practice, temperatures normally in the range from about 10° to 100° C. are suitable, especially if dimethyl formamide or dimethyl sulfoxide is employed as solvent. The preferred temperature range is from 20° to 60° C.

Suitable strong bases are, in particular, the hydroxides, amides and alcoholates (preferably those of primary alcohols containing 1 to 4 carbon atoms) of alkali metals, those of lithium, sodium and potassium being of principal interest for economic reasons. In principle, however, and in special cases, it is also possible to use with success alkali metal sulfides and alkali metal carbonates, aryl alkali compounds, e.g. phenyllithium, or strongly basic amines (including ammonium bases), e.g. trialkylammonium hydroxides.

The novel compounds defined above exhibit a more or less pronounced fluorescence in the dissolved or finely divided state. They can be used for whitening and/or brightening a wide variety of synthetic, regenerated man-made or natural organic materials or substances which contain such organic materials.

Without any restriction being implied by the following classification, examples of organic materials which can be treated with fluorescent whitening agents are:

I. Man-made organic material of high molecular weight:

(a) polymerisation products based on organic compounds containing at least one polymerisable carbon-carbon double bond, that is to say their homopolymers of copolymers as well as their aftertreatment products, for example, crosslinking, grafting or degradation products, polymer blends, or products obtained by modification of reactive groups, for example polymers based on α,β-unsaturated carboxylic acids or derivatives of such carboxylic acids, especially on acrylic compounds, for example acrylates, acrylic acid, acrylonitrile, acrylamides and their methacrylic analogues, of olefin hydrocarbons (for example ethylene, propylene, styrenes or dienes and also ABS polymers), and polymers based on vinyl and vinylidene compounds (for example vinyl chloride, vinyl alcohol and vinylidene chloride);

(b) polymerisation products which can be obtained by ring opening, for example, polyamides of the polycaprolactam type, and also polymers which are obtained both by polyaddition and by polycondensation, for example polyethers or polyacetals;

(c) polycondensation products or precondensates based on bifunctional or polyfunctional compounds with condensable groups, their homocondensation and co-condensation products, and aftertreatment products, for example polyesters, especially saturated polyesters (for example ethylene glycol, terephthalic acid polyester) or unsaturated polyesters (for example maleic acid-dialcohol polycondensates as well as their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, their precondensates and and analogues, polycarbonates and silicones;

(d) polyadducts, such as polyurethanes (crosslinked and uncrosslinked) and epoxy resins.

II. Regenerated man-made organic material, for example, cellulose esters of varying degrees of esterification (so-called 2½-acetate or triacetate) or cellulose ethers, regenerated cellulose (viscose or cuprammonium cellulose), or their aftertreatment products, and casein plastics.

III. Natural organic material of animal or vegetable origin, for example based on cellulose or proteins, such as cotton, wool, linen, silk, natural film-forming resins, starch and casein.

The organic material to be whitened and/or brightened can be in the most diverse states of processing (raw materials, semi-finished goods or finished goods). On the other hand, it can be in the form of structures of the most diverse shapes, for example predominantly three-dimensional structures such as sheets, profiles, injection mouldings, various machined articles, chips, granules or foams, and also predominantly two-dimensional structures, such as films, sheets, lacquers, coatings and impregnations; or predominantly one dimensional bodies such as filaments, fibres, flocks and wires. The above materials can, on the other hand, also be in an unshaped state, in the most diverse homogeneous or inhomogeneous forms of division, as for example in the form of powders, solutions, emulsions, dispersions, latices, pastes or waxes.

Fibrous material can be, for example, in the form of endless filaments (stretched or unstretched), staple fibres, flocks, hanks, textile filaments, yarns, threads, nonwovens, felts, waddings, flocked structures or woven textile or bonded textile fabrics, knitted fabrics, and papers, cardboards or paper pulps.

The compounds to be used in the practice of this invention are of importance, inter alia, for the treatment of organic textile fabric, especially woven textile fabrics. If it is intended to whiten fibres which can be in the form of staple fibres or endless filaments or in the form of hanks, woven fabrics, knitted fabrics, fleeces, flocked substrates or bonded fabrics, this is advantageously effected in an aqueous medium in which the compounds of the invention are finely dispersed (suspensions, so-called microdispersions, or, optionally, solutions). If desired, dispersing agents, stabilisers, wetting agents and further assistants can be added during the treatment.

Depending on the type of fluorescent whitening agent used, it can be advantageous to carry out the treatment in a neutral or alkaline or acid bath. The treatment is usually carried out in the temperature range from 20° to 140° C., for example at the boiling point of the bath or near it (about 90° C.).

Solutions or emulsions in organic solvents can also be used for the finishing according to the invention of textile substrates, as is practised in the dyeing industry in so-called solvent dyeing (pad-thermofixation application, or exhaust dyeing methods in dyeing machines).

The fluorescent whitening agents of the present invention can further be added to, or incorporated in, the materials before or during their shaping. They can thus be added to the moulding or injection moulding compound in the manufacture of films, sheets (e.g. rolling into polyvinyl chloride at elevated temperature) or moulded articles.

If man-made or regenerated man-made organic materials are formed by spinning processes or from spinning solutions/melts, the fluorescent whitening agents can be applied by the following methods:

addition to the starting materials (for example monomers) or intermediates (for example precondensates or prepolymers), that is to say before or during the polymerisation, polycondensation or polyaddition, sprinkling in powder form on polymer chips or granules for spinning solutions/melts;

bath dyeing of polymer chips or granules for spinning solutions/melts;

metered addition to spinning melts or spinning solutions; and application to the spun tow before stretching. The fluorescent whitening agents of the present invention can also be employed e.g. in the following formulations:

(a) in mixtures with dyes (shading) or pigments (coloured pigments or especially, for example, white pigments), or as an additive to dyebaths, printing pastes, discharge pastes or reserve pastes, or for the aftertreatment of dyeings, prints or discharge prints;

(b) in mixtures with carriers, wetting agents, plasticisers, swelling agents, antioxidants, ultraviolet absorbers, heat stabilisers and chemical bleaching agents (chlorite bleach or bleaching bath additives);

(c) in admixture with crosslinking agents or finishing agents (for example starch or synthetic finishes), and in combination with a wide variety of textile finishing processes, especially synthetic resin finishes (for example creaseproof finishes such as wash-and-wear, permanent-press or non-iron), as well as flameproof finishes, soft finishes, anti-soiling finishes or antistatic finishes, or antimicrobial finishes;

(d) incorporation of the fluorescent whitening agent in polymer carriers (polymerisation, polycondensation or polyaddition products, in dissolved or dispersed form, for use e.g. in coating agents, impregnating agents or binders (solutions, dispersions and emulsions) for textiles, nonwovens, papers and leather;

(e) as additives to master batches;

(f) as additives to a wide variety of industrial products in order to render these more marketable (for example improving the appearance of soaps, detergents, pigments);

(g) in spinning bath preparations, that is to say as additives to spinning baths which are used for improving the slip for the further processing of synthetic fibres, or from a special bath before the stretching of the fibre;

(h) as scintillators for various purposes of a photographic nature, for example for electrophotographic reproduction or supersensitising;

(i) depending on the substitution, as laser dyes.

The compounds of the invention can also be employed in combination with other fluorescent whitening agents. Examples of suitable compounds which can be mixed with the compounds of the invention are: 1,4-bis-(benzoxazol-2'-yl)-naphthalene, 4,4'-bis-(ethoxycarbonylvinyl)-stilbene, 4,4'-bis-(cyanovinyl)-stilbene, 1,4-bis(2'-cyanostyryl)-benzene, 1,5-bis-(benzoxazole-2'-yl)-thiophene, 1-phenyl-4-(5',7'-dimethylbenzoxazol-2'-yl)-stilbene, 1,2-bis-(5'-methylbenzoxazol-2'-yl)-vinylene, 4-(benzoxazol-2'-yl)-4'-(3''-methyl-1'',2'',4''-oxadiazol-5''-yl)-stilbene and 2,4-dimethoxytriazine-6-yl-pyrene.

The fluorescent whitening agent mixtures so obtained contain the compound of the invention and the known compound in the ratio of 1:9 to 9:1, preferably 1:2 or 2:1.

If the whitening process is combined with textile treatment or finishing methods, the combined treatment can in many cases advantageously be carried out with the aid of appropriate stable preparations which contain the fluorescent whitener compounds in a concentration such that the desired white effect is achieved.

In certain cases, the fluorescent whitening agents are made fully effective by an aftertreatment. This can be, for example, a chemical treatment (for example acid treatment), a thermal treatment or a combined chemical/thermal treatment. Thus, for example, the appropriate procedure to follow in whitening a number of fibre substrates, for example polyester fibres, with the fluorescent whitening agents of the present invention, is to impregnate these fibres with the aqueous dispersions (or optionally also solutions) of the whitening agents at temperatures below 75° C., for example at room temperature, and to subject them to a dry heat treatment at temperatures above 100° C., it being generally advisable additionally to dry the fibrous material beforehand at a moderately elevated temperature, for example in the range from at least 60° C. to about 130° C. The heat treatment in the dry state is then advantageously carried out at a temperature between 120° and 225° C., for example by heating in a drying chamber, by ironing within the specified temperature range or by treatment with dry, superheated steam. The drying and dry heat treatment can also be carried out in immediate succession or be combined in a single procedure.

The amount of fluorescent whitening agent of the present invention to be used, based on the weight of the material to be whitened, can vary within wide limits. A marked and lasting effect can be obtained even with very insignificant amounts, in certain cases 0.0001 percent by weight. But it is also possible to use amounts of up to 0.8 percent by weight and on occasion, up to 2 percent by weight. For most practical purposes, it is preferred to use amounts between 0.0005 and 0.5 percent by weight.

For various reasons it is often advantageous not to use the fluorescent whitening agents by themselves, i.e. pure, but in admixture with a wide variety of assistants and extenders for example anhydrous sodium sulfate, sodium sulfate decahydrate, sodium chloride, sodium carbonate, alkali metal phosphates, such as sodium or potassium othophosphate, sodium or potassium pyrophosphate and sodium or potassium tripolyphosphates or alkali metal silicates.

The invention is illustrated by the following Examples, in which percentages are by weight. Melting and boiling points are uncorrected, unless otherwise indicated.

EXAMPLE 1

With stirring, 6.5 g of the aldehyde of the formula

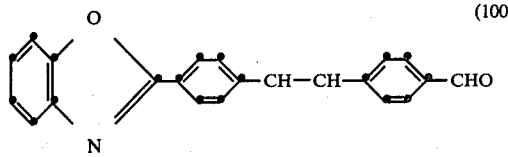 (100)

are suspended at room temperature in 200 ml of ethylene glycol monomethyl ether. 2.1 g of O-methylhydroxylamine hydrochloride are dissolved in 10 ml of water and this solution is then added to the suspension of the aldehyde. Then 2.1 g of sodium acetate are added, the temperature of the suspension rising from 25° to 28° C. The reaction mixture is stirred for 6 hours at room temperature, then filtered with suction. The filter cake is washed with water and vacuum dried at 60° C. Two recrystallisations from 200 ml of chlorobenzene and 200 ml of toluene with the aid of fuller's earth yields 3.9 g of the compound of the formula

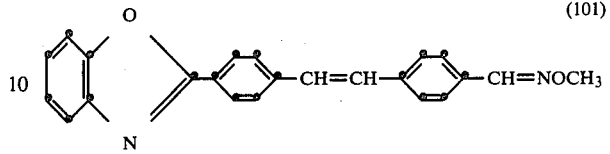 (101)

in the form of pale yellow crystals with a melting point of 247°–248° C.

The compounds of the formula

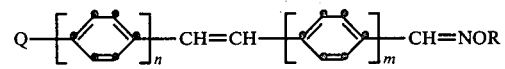

are obtained in similar manner:

| Compound | Q | n | m | R | Melting point °C. |
|---|---|---|---|---|---|
| 102 | 4,7-dimethylbenzoxazol-2-yl (CH₃ at 4 and 7) | 1 | 1 | —CH₃ | 165–166 |
| 103 | 5-tert-butylbenzoxazol-2-yl | 1 | 1 | —CH₃ | 239–240 |
| 104 | 4-methylbenzoxazol-2-yl | 1 | 1 | —CH₃ | 191–193 |
| 105 | 7-methylbenzoxazol-2-yl | 1 | 1 | —CH₃ | 166–168 |
| 106 | 5-methylbenzoxazol-2-yl | 1 | 1 | —CH₃ | 285–286 |

-continued

| Compound | Q | n | m | R | Melting point °C. |
|---|---|---|---|---|---|
| 107 | benzoxazole-2-yl with CH₃OOC substituent | 1 | 1 | —CH₃ | 271–272 |
| 108 | NC—CH=CH— | 1 | 1 | —CH₃ | 137–138 |
| 109 | benzoxazol-2-yl | 1 | 1 | —C₂H₅ | 187–188 |
| 110 | benzoxazol-2-yl | 1 | 1 | C₄H₉(n) | 172–173 |
| 111 | benzoxazol-2-yl | 1 | 1 | —CH(CH₃)₂ | 253–254 |
| 112 | benzoxazol-2-yl | 1 | 1 | —CH(C₂H₅)(CH₃) | 247–248 |
| 113 | benzoxazol-2-yl | 1 | 1 | —CH₂—CH=CH₂ | 181–182 |
| 114 | benzoxazol-2-yl | 1 | 1 | —CH₂CH₂OCH₃ | 171–172 |
| 115 | oxazolopyridin-2-yl | 1 | 1 | —C₂H₅ | 255–256 |
| 116 | oxazolopyridin-2-yl | 1 | 1 | —C₄H₉(n) | 273–274 |

-continued

| Compound | Q | n | m | R | Melting point °C. |
|---|---|---|---|---|---|
| 117 | 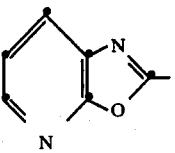 | 1 | 1 | —CH(CH$_3$)$_2$ | 267–168 |
| 118 | 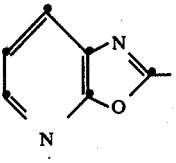 | 1 | 1 | —CH(C$_2$H$_5$)(CH$_3$) | 260–261 |
| 119 | NC—CH=CH— | 1 | 1 | —C$_4$H$_9$(n) | 118–119 |
| 120 | NC—CH=CH— | 1 | 1 | —C$_2$H$_5$ | 155–156 |
| 121 | NC—CH=CH— | 1 | 1 | —CH(CH$_3$)$_2$ | 140–141 |
| 122 | NC—CH=CH— | 1 | 1 | —CH(C$_2$H$_5$)(CH$_3$) | 151–152 |
| 123 | NC—CH=CH— | 1 | 1 | —CH$_2$CH$_2$OCH$_3$ | 129–130 |
| 124 | NC—CH=CH— | 1 | 1 | —CH$_2$—C≡CH | 158–159 |
| 125 | NC—CH=CH— | 1 | 1 | —CH$_2$—CH=CH$_2$ | 123–124 |
| 126 | 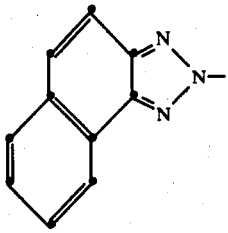 | 1 | 1 | —CH$_3$ | 188–189 |
| 127 | 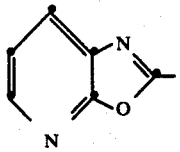 | 1 | 1 | —CH$_3$ | 237–238 |
| 128 | NC—CH=CH— | 1 | 1 | —CH$_2$CH$_2$CN | 128–129 |
| 129 | NC—CH=CH— | 1 | 1 | —CH$_2$COOC$_2$H$_5$ | 131–132 |
| 130 | 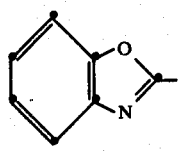 | 1 | 1 | —CH$_2$CH$_2$CN | 253 (decomp.) |
| 131 | 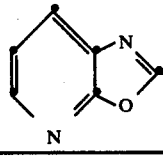 | 1 | 1 | —CH$_2$CH$_2$CN | 277–278 |

PREPARATION OF THE STARTING
MATERIAL OF THE FORMULA (100)

With stirring, 13.4 g of terephthaldehyde are suspended at room temperature in 60 ml of methanol. To this suspension are then added 36 g of a 30% methanolic solution of sodium methylate. The ensuing reaction is exothermic and the temperature is kept at 20°–22° C. by gentle cooling. To the resultant golden yellow solution is added dropwise a solution of 34.5 g of the phosphonate of the formula

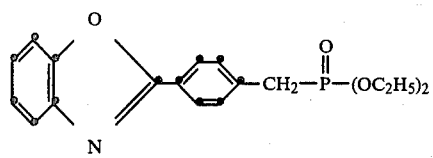
(109)

in 100 ml of methanol over 20 minutes. The suspension so obtained is stirred for 4½ hours at room temperature and filtered with suction. The filter cake is washed well with methanol and dried at 60° C., affording 20 g of the compound of the formula (100) with a melting point of 231°–232° C.

The aldehydes of the formula

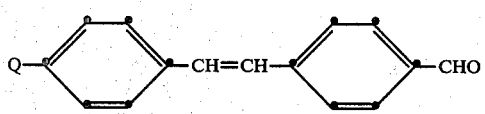

are obtained in similar manner:

| Compound | Q | Melting point °C. |
|---|---|---|
| 132 | 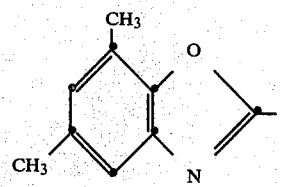 | 193–195 |
| 133 | 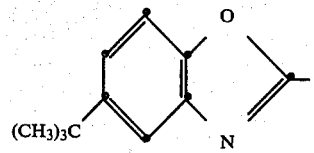 | 210–213 |
| 134 | 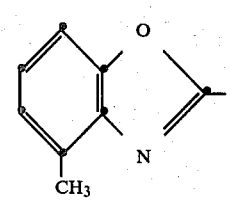 | 184–188 |
| 135 | 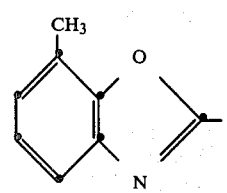 | 185–186 |
| 136 | 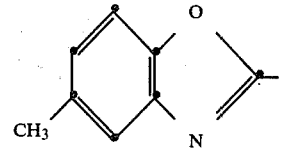 | 219–220 |
| 137 | 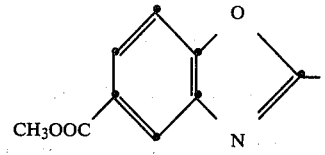 | 234–236 |
| 138 | NC—CH=CH— | 154–156 |
| 139 | 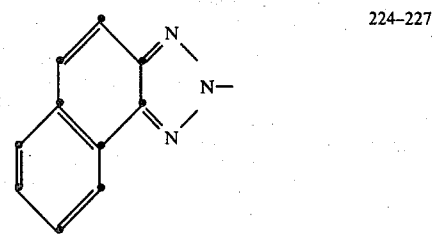 | 224–227 |
| 140 | 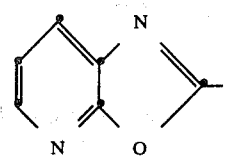 | 254–264 |

The phosphonates employed are known or they may be obtained in per se known manner, e.g. as described in U.S. Pat. Nos. 4,261,855 and 4,208,513 or in European patent application No. 31796.

EXAMPLE 2

With stirring 3.8 g of 2-[(4-diethoxyphosphorylmethyl)-4-phenyl]-1,3,4-oxdiazol-2-one (q.v. European patent 9095) and 1.7 g of the aldehyde of the formula

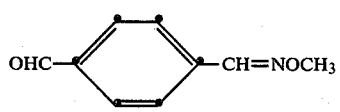
(200)

are dissolved at 40° C. in 20 ml of dimethyl formamide. To this solution are then added 2 g of a 30% methanolic solution of sodium methylate. The reddish brown solution is stirred for 2 hours at 40° C., diluted with 40 ml of methanol, and then cooled to 5° C. The crystallised precipitate is filtered with suction and vacuum dried at 70° C. Recrystallisation from 100 ml of petroleum distillate with a boiling point of 110°–150° C. and from 100 ml of xylene with the aid of fuller's earth yields 1.2 g of the compound of the formula

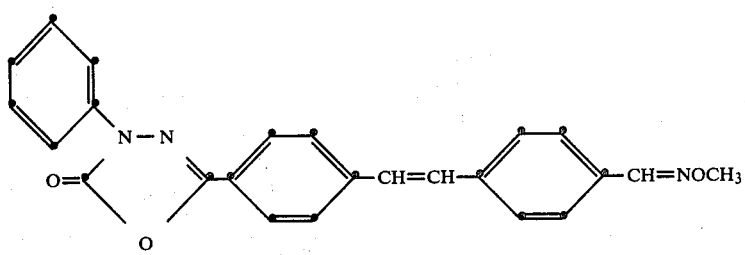
(201)

in the form of a yellow powder with a melting point of 185°–186° C.

The aldehyde of the formula (200) may be obtained as follows:

With stirring, 24 g of p-toluylaldehyde are dissolved in 240 ml of 2-methoxyethanol at room temperature. To this solution are added a solution of 20.8 g of O-methylhydroxylamine hydrochloride in 20 ml of water and a solution of 20.5 g of sodium acetate in 20 ml of water. The reaction mixture is then stirred for 20 hours at room temperature, poured into 600 ml of water, and extracted with 400 ml of toluene. After thorough shaking, the organic phase is separated and dried over anhydrous sodium sulfate. The solvent is then distilled off, affording 28.3 g of the compound of the formula

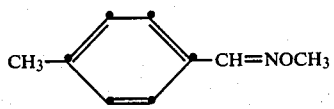
(202)

in the form of a pale brownish oil (purity 96.6%).

With stirring, 28.3 g of the compound of the formula (202), 35.5 g of N-bromosuccinimide and 0.5 g of dibenzoyl peroxide are heated slowly in 430 ml of carbon tetrachloride, while simultaneously irradiating with a 500 watt halogen lamp. A vigorous reaction, which lasts about 2 minutes, commences at 76° C. The suspension is refluxed for 2 hours, cooled to room temperature and extracted with 500 ml of water. The organic phase is separated and dried over anhydrous sodium sulfate. The solvent is distilled off and the residue congeals to a crystalline mass, affording 42 g of the compound of the formula

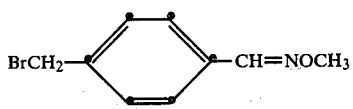
(203)

with a melting point of 70°–71° C.

With stirring, 34.7 g of 2-nitropropane and 54 g of a 30% methanolic solution of sodium methylate are added dropwise to 500 ml of methanol and the mixture is stirred for 1 hour. Then 68.4 g of compound (203) are added and the reaction mixture is warmed to 45° C. and stirred for 1 hour at this temperature and for about 20 hours at room temperature. The reaction mixture is then concentrated and the residue is purified by column chromatography over silica gel with toluene as eluant. Yield: 31.2 g of the aldehyde of the formula (200) with a melting point of 66°–67° C.

The compounds of the formula

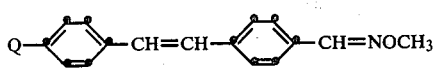

are obtained in the same way as described at the outset of this Example:

| Compound | Q | Melting point (°C.) |
|---|---|---|
| 204 | | 236–237 |
| 205 | | 271–273 |
| 206 | | 212–213 |
| 207 | | 181–182 |
| 208 | | 169–170 |
| 209 | | 196–197 |

-continued

| Compound | Q | Melting point (°C.) |
|---|---|---|
| 210 | 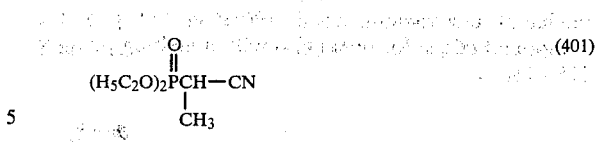 | 155–156 |
| 211 | | 234–235 |
| 212 | | 207–208 |
| 213 | | 244–245 |

EXAMPLE 3

With stirring, 4.7 g of stilbene-4,4'-dialdehyde are dissolved at 60° C. in 200 ml of 2-methoxyethanol. To this solution are then added a solution of 5 g of O-methylhydroxylamine hydrochloride in 10 ml of water and a solution of 5 g of sodium acetate in 10 ml of water. The reaction mixture is stirred for 1 hour at 60° C. and for about 20 hours at room temperature. The crystallised product is filtered with suction and recrystallised 4 times from 2-methoxyethanol and twice from xylene with the aid of fuller's earth, giving 0.4 g of the compound of the formula

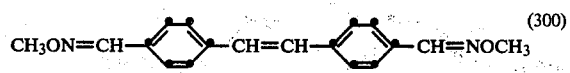
(300)

in the form of greenish crystal needles with a melting point of 190°–191° C.

EXAMPLE 4

With stirring, 6.7 g of the aldehyde of the formula

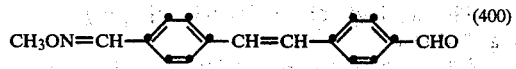
(400)

and 4.8 g of the phosphonate of the formula $$(H_5C_2O)_2\overset{O}{\underset{\underset{CH_3}{|}}{\overset{\|}{P}}}CH-CN \quad (401)$$

are dissolved at 65° C. in a mixture of 200 ml of dimethyl formamide and 100 ml of N-methylpyrrolidone. Then 5.4 g of a 30% methanolic solution of sodium methylate are added dropwise over 10 minutes and the mixture is stirred for 20 hours at room temperature and filtered. The product is precipitated from the filtrate by addition of 300 ml of water, isolated by filtration, stirred in 200 ml of methanol, isolated once more and recrystallised twice from 70 ml of toluene with the aid of fuller's earth, affording the compound of the formula

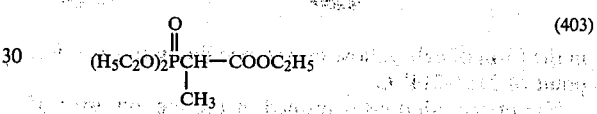
(402)

in the form of pale yellow crystals with a melting point of 162°–163° C.

Transesterification of the compound obtained when using instead of the phosphonate of the formula (401) that of the formula $$(H_5C_2O)_2\overset{O}{\underset{\underset{CH_3}{|}}{\overset{\|}{P}}}CH-COOC_2H_5 \quad (403)$$

yields the compound of the formula

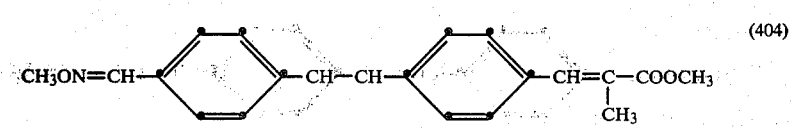
(404)

with a melting point of 163°–164° C.

The aldehyde of the formula (400) may be obtained as follows:

With stirring, 42 g of the compound of formula (203) and 91 g of trimethylphosphite are heated to about 110° C. and stirred for about 20 hours at this temperature. Excess trimethylphosphite is then distilled off under a water jet vacuum and the residue is purified by column chromatography over silica gel. Eluant: first toluene/ethyl acetate (9:1) and then ethyl acetate. Yield: 35.5 g of the phosphonate of the formula

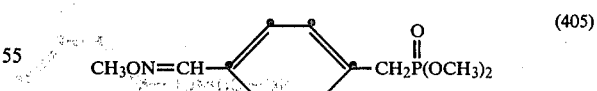
(405)

in the form of a golden yellow oil.

With stirring, 13.4 g of terephthalaldehyde are suspended at room temperature in 60 ml of methanol. To this suspension are added 18 g of a 30% methanolic solution of sodium methylate, whereupon a yellow solution is obtained. Then a solution of 25.7 g of the phosphonate of the formula (405) in 60 ml of methanol is added dropwise at 18°–20° C. and the reaction mixture is stirred for 20 hours at room temperature. The crystallised product is filtered with suction, washed with methanol and vacuum dried, affording 12.8 g of the compound of the formula (400) with a melting point of 115°–118° C.

with methanol and recrystallised from two 400 ml portions of chlorobenzene with the aid of fuller's earth, affording 2.5 g of the compound of the formula

(602)

EXAMPLE 5

With stirring, 5.1 g of the phosphonate of the formula (405) and 3.9 g of methyl 4-formylcinnamate are dissolved at 40° C. in 60 ml of dimethyl formamide. To this solution are added 4 g of a 30% methanolic solution of sodium methylate and the mixture is stirred for 2 hours at 60° C. The reaction mixture is poured into 240 ml of methanol and the crystallised product is filtered with suction, washed with methanol and vacuum dried at 80° C. Three recrystallisations from toluene with the aid of fuller's earth yield 2.3 g of the compound of the formula in the form of pale yellow crystals with a melting point of 246°–247° C.

The aldehyde of the formula (600) may be obtained as follows:

With stirring, 12.6 g of biphenyl-4,4'-dialdehyde and 11 g of sodium methylate are suspended at room temperature in 40 ml of methanol. The phosphonate of the formula (405) is dissolved in 40 ml of methanol and added dropwise to the above suspension over 40 minutes. The reaction mixture is stirred for about 20 hours and then filtered. The filter cake is washed with methanol and vacuum dried at 80° C., affording 12.5 g of the aldehyde of the formula (600) with a melting point of 134°–136° C.

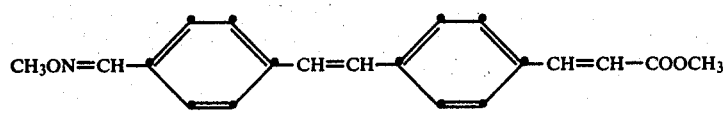

(500)

in the form of pale yellow crystal needles with a melting point of 213°–214° C.

Use of the ethyl ester instead of the methyl ester of 4-formylcinnamic acid and of sodium ethylate as condensing agent, gives the compound of the formula

EXAMPLE 7

With stirring, 6.7 g of the aldehyde of the formula

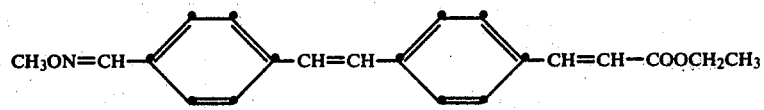

(501)

in the form of pale yellow crystals with a melting point of 209°–210° C.

EXAMPLE 6

With stirring, 6.8 g of the aldehyde of the formula

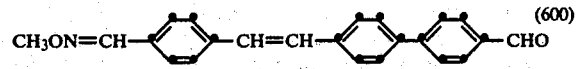

(600)

and 3.5 g of the phosphonate of the formula

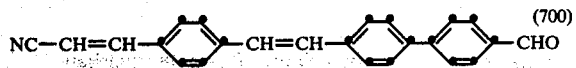

(700)

are dissolved at 70° C. in 300 ml of 2-methoxyethanol. Then 2.5 g of O-methylhydroxylamine hydrochloride and 2.5 g of sodium acetate are each dissolved in 5 ml of water and both solutions are added. The batch is stirred for 6 hours at room temperature and the crystallised product is filtered with suction, dried, and recrystallised from 70 ml of chlorobenzene with the aid of fuller's earth. Yield: 1.5 g of the compound of the formula

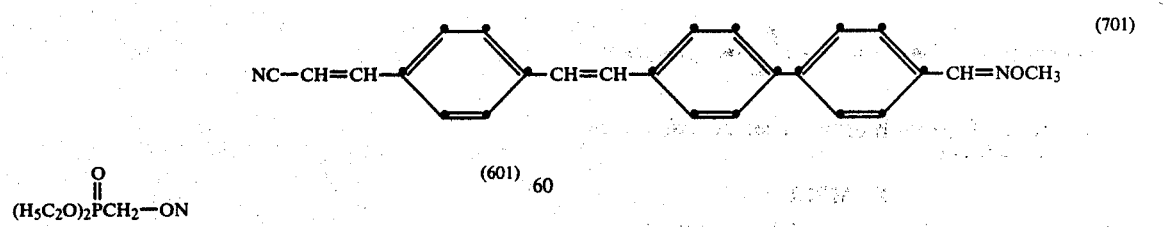

(701)

$$(H_5C_2O)_2\overset{O}{\overset{\|}{P}}CH_2-ON$$

(601)

are dissolved at 50° C. in 150 ml of N-methylpyrrolidone. To this solution are added 4 g of a 30% methanolic solution of sodium methylate and the batch is stirred for about 20 hours at room temperature. The filtered solution is diluted with 300 ml of methanol and the crystallised product is filtered with suction, washed in the form of pale yellow crystals with a melting point of 236°–237° C.

The aldehyde of the formula (700) may be prepared as follows:

8.4 g of biphenyl-4,4'-dialdehyde and 7.2 g of a 30% methanolic solution of sodium methylate are stirred into 60 ml of methanol. Then 10 g of 4-(dimethoxyphosphorylmethylphenyl)cinnamonitrile are dissolved in 60 ml of methanol and this solution is then added dropwise at room temperature over 40 minutes. The batch is stirred for 20 hours at room temperature, then cooled to 0° C. The crystallised product is filtered with suction, washed copiously with methanol and vacuum dried. Yield: 6.7 g of the compound of the formula (700) with a melting point of 127°–131° C.

The 4-(dimethoxyphosphorylmethylphenyl)cinnamonitrile may be prepared as follows:

390 g of 4-bromomethylcinnamonitrile are suspended in 600 ml of trimethylphosphite and the suspension is added in portions to 250 ml of well stirred trimethylphosphite of 90° C., such that the strongly exothermic reaction can be kept under control. Excess trimethylphosphite is then distilled off under a water jet vacuum and 330 ml of toluene and 660 ml of hexane are added to the residue, which is cooled to 0° C. The crystallised product is filtered with suction and vacuum dried at 50° C., affording 427 g of 4-(dimethoxyphosphorylmethylphenyl)cinnamonitrile with a melting point of 98°–101° C.

EXAMPLE 8

With stirring, 5 g of 4-(dimethoxyphosphorylmethylphenyl)cinnamonitrile and 3.6 g of the aldehyde of the formula

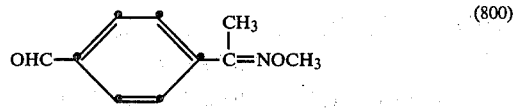

are dissolved in 50 ml of dimethyl formamide. Then 4 g of a 30% methanolic solution of sodium methylate are added dropwise over 15 minutes. The batch is stirred for 2 hours at 40° C., diluted with 250 ml of methanol, and cooled to 5° C. The crystallised product is filtered with suction and vacuum dried. Recrystallisation from toluene with the aid of fuller's earth yields 2.7 g of the compound of the formula

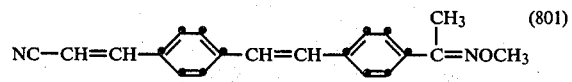

in the form of pale yellow crystal flakes with a melting point of 168°–169° C.

The compounds of the formulae

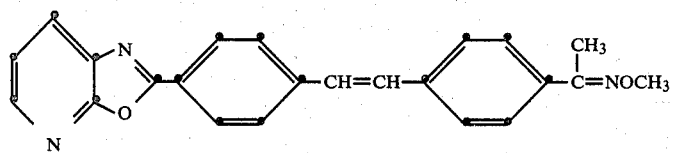

(pale yellow crystal flakes, m.p. 245°–246° C.) and (pale yellow crystal flakes, m.p. 239°–240° C.) may be obtained in similar manner.

The aldehyde of the formula (800) may be prepared as follows:

134 g of 4-methylacetophenone are stirred at room temperature into 2000 ml of 2-methoxyethanol. A solution of 100 g of O-methylhydroxylamine hydrochloride in 200 ml of water and a solution of 98 g of sodium acetate in 200 ml of water are then added. The reaction mixture is stirred for 24 hours at room temperature, poured into 800 ml of water and extracted with 200 ml of ether. The ethereal phase is separated and dried over anhydrous sulfate and concentrated, affording 153.2 g of the compound of the formula

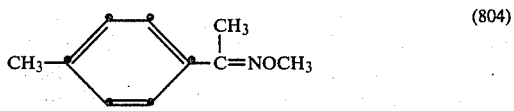

in the form of a pale yellow liquid.

With stirring and irradiation with a 500 watt halogen lamp, 153 g of the compound of the formula (804), 178 g of N-bromosuccinimide and 5 g of dibenzoyl peroxide are slowly heated to reflux in 1500 ml of carbon tetrachloride and refluxed for 6 hours. The reaction mixture is then filtered hot and the filtrate is cooled and extracted with 1500 ml of water. The extract is dried over sodium sulfate and concentrated. The residue is purified over a column of silica gel with toluene as eluant, affording 190 g of the compound of the formula

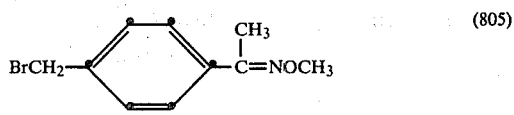

in the form of a yellow liquid in 56% purity (gas chromatography). 141 g of a 30% methanolic solution of sodium methylate are stirred into 1500 ml of absolute ethanol. Then 89 g of 2-nitropropane are added dropwise and the mixture is stirred for 1 hour at room temperature. Then 190 g of the compound of the formula (805) are added and the temperature rises to 36° C. The reaction mixture is further stirred for 4 hours at room temperature, then concentrated and the residue is purified over a column of silica gel using first hexane/toluene (1:1) and then toluene as eluant. Yield: 70 g of the aldehyde of the formula (800) in the form of a pale brown oil in 92.5% purity (gas chromatography).

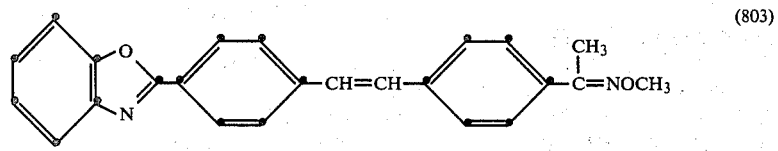

EXAMPLE 9

Polyester fabric (Terylene ® 540) is padded at room temperature with a liquor which contains 1 g/l of the compound of the formula (101), (102), (103) or (108), and 1 ml of the condensation product of 8-9 moles of ethylene oxide and 1 mole of p-tert-octylphenol. The liquor pick-up is 80%. The fabric is then dried for 10 minutes at 80° C. and subsequently thermofixed at 220° C. for 30 seconds. A good white effect is obtained on the treated fabric.

EXAMPLE 10

Polyester fabric (Terylene ® 540) is padded at room temperature with a liquor which contains 1 g/l of the compound of the formula (108), and 1 ml of the condensation product of 8-9 moles of ethylene oxide and 1 mole of p-tert-octylphenol. The liquor pick-up is 80%. The fabric is then dried for 10 minutes at 80° C. and subsequently thermofixed at 200° C. for 30 seconds. A good white effect is obtained on the treated fabric.

EXAMPLE 11

Polyester fabric (Terylene ® 540) is treated in a dyeing machine, at a liquor ratio of 1:20, with an aqueous bath which contains 0.1%, based on the weight of the goods, of the compound of the formula (101), (102), (104), (106) or (108), and 1 g/liter of the condensation product of 35 moles of ethylene oxide and 1 mole of stearyl alcohol. The bath is then heated from 40° to 120° C. in the course of 30 minutes, kept at this temperature for 30 minutes, and then cooled to 15° C. in the course of 15 minutes. The fabric is then rinsed in running deionised water and dried at 70° C. An excellent white effect is obtained on the treated fabric.

EXAMPLE 12

Polyamide 6.6 woven jersey fabric is treated in a dyeing machine, at a liquor ratio of 1:20, with an aqueous bath which contains 0.2%, based on the weight of the goods, of the compound (101), (102), (104), or (106), and 3 g/liter of a mixture of 60 parts by weight of sodium hydrosulfite and 40 parts by weight of sodium pyrophosphate. The bath is heated from 40° to 130° C. in the course of 30 minutes, kept at this temperature for 30 minutes and then cooled to 15° C. in the course of 15 minutes. The fabric is then rinsed in running deionised water and dried at 60° C. A good white effect is obtained on the treated polyamide fabric.

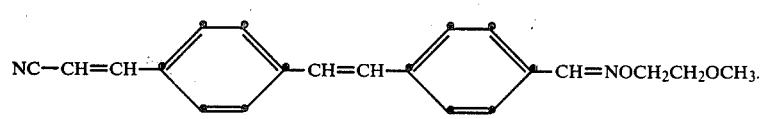

7. The stilbene compound according to claim 5 of the formula
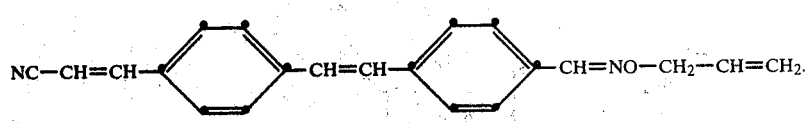

What is claimed is:

1. A stilbene compound of the formula

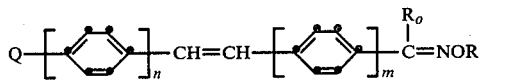

wherein Q is hydrogen; benzoxazolyl; benzimidazolyl; v-triazolyl; 1,3,4-oxdiazolyl; pyrimidyl; pyridazinonyl; pyrazinyl; s-triazinyl; 1,3,4-oxdiazolonyl; 1,2,4-oxdiazolyl; pyrazolyl; isoxazolyl; benzisoxazolyl; oxazolo[5,4-b]pyridyl; oxazolo[5,4-e]pyridyl; 1,2,4-triazolo[1,5-a]pyridyl; —CH=C(R$_1$)(R$_2$), in which R$_1$ is hydrogen, C$_1$–C$_6$alkyl which is unsubstituted or substituted by non-chromophoric groups, and R$_2$ is alkoxycarbonyl containing altogether 2 to 7 carbon atoms, cyano, carboxyl, carbamoyl, phosphonic acid dialkyl ester, C$_1$–C$_6$alkyl or arylsulfonyl; or

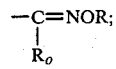

R$_0$ is hydrogen or C$_1$–C$_6$alkyl; R is C$_1$–C$_6$alkyl which is unsubstituted or substituted by non-chromophoric groups, C$_2$–C$_5$alkenyl, C$_2$–C$_5$alkynyl, di(C$_1$–C$_4$)alkylamino(C$_1$–C$_4$)alkyl, C$_1$–C$_4$hydroxyalkyl, C$_1$–C$_4$phenylalkyl or cycloalkyl containing 5 to 12 ring members; and each of m and n independently of the other is 1 or 2.

2. A stilbene compound according to claim 1 of the formula

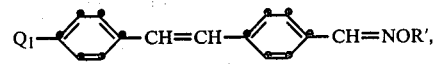

wherein R' is C$_1$–C$_4$alkyl, C$_1$–C$_4$cyanoalkyl, C$_1$–C$_4$alkoxy-C$_2$–C$_4$alkyl, C$_3$–C$_4$alkenyl, C$_3$–C$_4$alkynyl or R$_x$OOC—C$_1$–C$_4$alkyl, in which R$_x$ is hydrogen or C$_1$–C$_4$alkyl, and Q$_1$ is phenyl or the radical —CH=C(R$_1$')(R$_2$'),

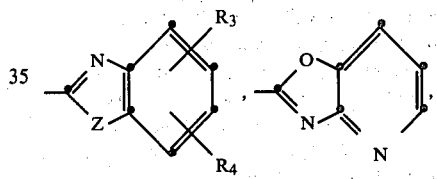

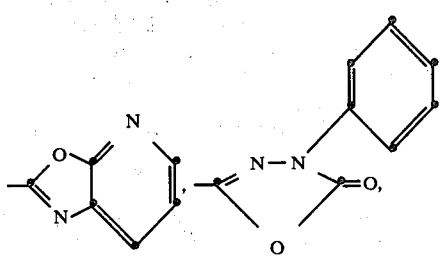

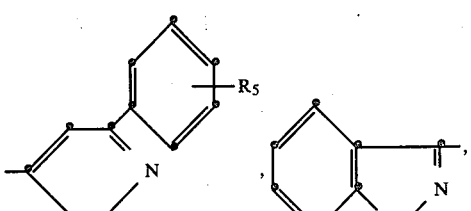

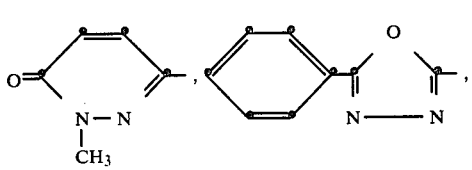

-continued

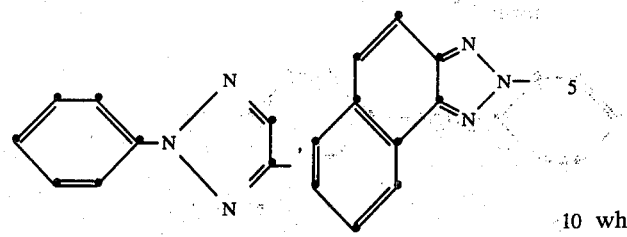

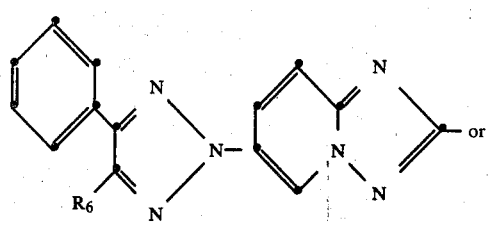

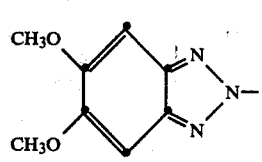

wherein $R_1'$ is hydrogen or $C_1$-$C_4$alkyl, $R_2'$ is alkoxycarbonyl containing altogether 2 to 5 carbon atoms, cyano, carboxyl, carbamoyl, $C_1$-$C_4$alkylsulfonyl or phenylsulfonyl, $R_3$ is hydrogen, chlorine, $C_1$-$C_4$alkyl, $C_1$-$C_3$phenylalkyl, cyclohexyl, phenyl, $C_1$-$C_4$alkoxy, $C_1$-$C_4$alkylsulfonyl, $C_2$-$C_5$alkoxycarbonyl, cyano or carboxyl or, together with $R_4$, is a fused cyclopentane, cyclohexane or benzene ring, each of which is unsubstituted or substituted by 1 to 4 methyl groups; $R_4$ is hydrogen, chlorine, $C_1$-$C_4$alkyl or $C_1$-$C_4$alkoxy or, together with $R_3$, is a fused cyclopentane, cyclohexane or benzene ring, each of which is unsubstituted or substituted by 1 to 4 methyl groups; $R_5$ is hydrogen or methoxy; $R_6$ is hydrogen, $C_1$-$C_4$alkyl or alkoxycarbonyl containing altogether 2 to 5 carbon atoms; and Z is O, S or NX, wherein X is hydrogen, $C_1$-$C_4$alkyl or phenyl.

3. A stilbene compound according to claim 2 of the formula

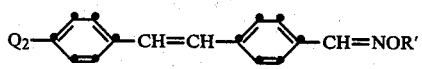

wherein R' is as defined in claim 2 and $Q_2$ is the radical —CH=C($R_1'$)($R_2''$),

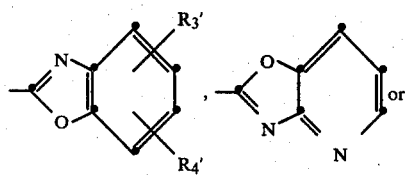

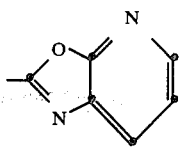

wherein $R_1'$ is hydrogen or $C_1$-$C_4$alkyl, $R_2''$ is alkoxycarbonyl containing altogether 2 to 5 carbon atoms or is cyano, $R_3'$ is hydrogen, $C_1$-$C_4$alkyl, $C_1$-$C_4$alkoxy or alkoxycarbonyl containing altogether 2 to 5 carbon atoms or, together with $R_4'$, is a fused benzene ring, and $R_4'$ is hydrogen or $C_1$-$C_4$alkyl or together with $R_3'$ is a fused benzene ring.

4. A stilbene compound according to claim 3 of the formula

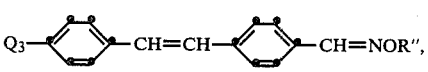

wherein R'' is $C_1$-$C_4$alkyl, $C_1$-$C_4$alkoxy-$C_2$-$C_4$alkyl or $C_3$-$C_4$alkenyl, and $Q_3$ is the radical —CH=CH—CN, —CH=CH—COO—$C_1$-$C_4$alkyl or the radical

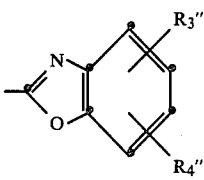

wherein $R_3''$ is hydrogen, $C_1$-$C_4$alkyl, $C_1$-$C_4$alkoxy or $C_2$-$C_5$alkoxycarbonyl, and $R_4''$ is hydrogen or $C_1$-$C_4$alkyl.

5. A stilbene compound according to claim 4 of the formula

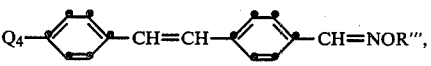

wherein R''' is —$CH_3$, —$C_2H_5$, —$CH_2CH_2OCH_3$ or —$CH_2$—CH=$CH_2$ and $Q_4$ is the radical —CH=CH—CN, —CH=CH—COO—$C_1$-$C_2$alkyl or

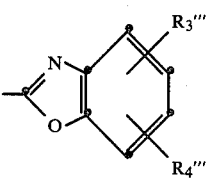

wherein $R_3'''$ is hydrogen or $C_1$-$C_4$alkyl and $R_4'''$ is hydrogen or $C_1$-$C_4$alkyl.

6. The stilbene compound according to claim 5 of the formula